(12) United States Patent
Anzai et al.

(10) Patent No.: US 8,299,277 B2
(45) Date of Patent: Oct. 30, 2012

(54) RADIATION PROTECTION DRUG CONTAINING TOCOPHEROL OR TOCOTRIENOL COMPOUND ESTER DERIVATIVE AS ACTIVE INGREDIENT

(75) Inventors: Kazunori Anzai, Chiba (JP); Megumi Ueno, Chiba (JP); Haruko Yakumaru, Chiba (JP); Junichi Ueda, Chiba (JP); Makoto Akashi, Chiba (JP); Shizuko Kobayashi, Chiba (JP); Jiro Takata, Fukuoka (JP); Nobuo Ikota, Chiba (JP)

(73) Assignees: National Institute of Radiological Sciences, Chiba (JP); Fukuoka University, Fukuoka (JP)

( * ) Notice: Subject to any disclaimer, the term of this patent is extended or adjusted under 35 U.S.C. 154(b) by 540 days.

(21) Appl. No.: 12/516,722

(22) PCT Filed: Nov. 14, 2007

(86) PCT No.: PCT/JP2007/072077
§ 371 (c)(1),
(2), (4) Date: Jun. 26, 2009

(87) PCT Pub. No.: WO2008/065891
PCT Pub. Date: Jun. 5, 2008

(65) Prior Publication Data
US 2010/0048512 A1    Feb. 25, 2010

(30) Foreign Application Priority Data
Dec. 1, 2006    (JP) .................. 2006-325408

(51) Int. Cl.
*C07D 311/00* (2006.01)
(52) U.S. Cl. ................ 549/407; 549/408; 549/410
(58) Field of Classification Search .......... 549/410, 549/407, 408
See application file for complete search history.

(56) References Cited

U.S. PATENT DOCUMENTS

| | | | | |
|---|---|---|---|---|
| 2,988,553 | A * | 6/1961 | Kussner et al. | ........ 549/410 |
| 6,703,384 | B2 * | 3/2004 | Sanders et al. | ........ 514/183 |
| 2003/0027857 | A1 | 2/2003 | Takata et al. | |

FOREIGN PATENT DOCUMENTS

| | | |
|---|---|---|
| JP | 01-121285 A | 5/1989 |
| JP | 10-072356 A | 3/1998 |
| JP | 2002-080475 A | 3/2002 |
| JP | 2003-267871 A | 9/2003 |
| JP | 2007-176879 A | 7/2007 |
| WO | 2004/026856 A1 | 4/2004 |

OTHER PUBLICATIONS

T. Sugawara et al, "Houshasen to Igaku", Kyoritsu Shuppan Co., Ltd., pp. 85-87, 1986.
C. Ostacolo, et al., "α-Tocopherol pro-vitamins: synthesis, hydrolysis and accumulation in rabbit ear skin", Journal of Controlled Release, 2004, pp. 403-413, vol. 99, No. 3.
C. Songthaveesin, et al., "Radio-protective effect of vitamin E on spermatogenesis in mice exposed to γ-irradiation: a flow cytometric study", Asian Journal of Andrology, 2004, pp. 331-336, vol. 6, No. 4.
Kazunori Anzai, et al., "In Vivo Radioprotection of Mice by 3-Methyl-1-phenyl-2-pyrazolin-5-one (Edaravone; Radicut $^R$), a Clinical Drug", J. Radiat. Res., 2004, pp. 319-323, vol. 45 No. 2.
Kazunori Anzai, et al., "Comparison of stable nitroxide, 3-substituted 2,2,5,5-tetramethylpyrrolidine-N-oxyls, with respect to protection from radiation, prevention of DNA damage, and distribution in mice", Free Radical Biology & Medicine, 2006, pp. 1170-1178, vol. 40.
International Search Report of PCT/JP2007/072077, mailed Dec. 25, 2007.

* cited by examiner

*Primary Examiner* — Noble Jarrell
*Assistant Examiner* — Raymond Covington
(74) *Attorney, Agent, or Firm* — Sughrue Mion, PLLC

(57) ABSTRACT

Administration of either a tocopherol represented by the general formula (1) or a tocotrienol compound ester derivative before or after exposure to radiation is effective in preventing or treating health disorders caused by the radiation exposure.

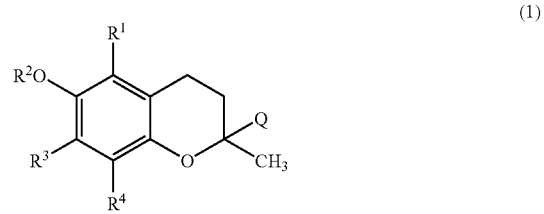

(1)

2 Claims, No Drawings

RADIATION PROTECTION DRUG CONTAINING TOCOPHEROL OR TOCOTRIENOL COMPOUND ESTER DERIVATIVE AS ACTIVE INGREDIENT

TECHNICAL FIELD

The present invention relates to the prevention and treatment of health disorders caused by exposure to radiation or cosmic rays, and protection against radiation injuries caused as side effects of radiodiagnosis or radiotherapy.

BACKGROUND ART

With the recent spread of measuring instruments and medical instruments which utilize radiation, persons who operate them and doctors and technical experts who conduct radiotherapy of cancer are always confronted with injury risk incurred by exposure to radiation. With an increase of the utilization of airplanes, carcinogenesis risk incurred by exposure to cosmic rays of aircrews and passengers is in question. In addition, carcinogenesis risk incurred by exposure to a slight amount of radiation of persons who undergo a medical examination by utilization of X-ray CT or the like is in question. On the other hand, it is pointed out that common persons may possibly be injured by exposure to radiation owing to an accident or terrorism connected with an atomic power station. Therefore, the development of a radiation protection drug for overcoming the risk of health disorders caused by exposure to radiation is an important social problem. However, very few radiation protection drugs for preventing and treating health disorders caused by exposure to radiation have been put to practical use (in the U.S.A., amifostine has been approved for preventing xerostomia in cancer radiotherapy in head-neck; J. Clin. Oncol. 18, 339 (2000)), and the development of a novel radiation protection drug is desired. Various aminothiols have been reported as radiation protection drugs for effective protection against health disorders caused by exposure to radiation (non-patent document 1). Shikita et al. have reported the effectiveness of heat-killed lactobacillus preparations as a radiation protection drug (Radiat. Res. 125, 293 (1991)), and Kagiya et al. have reported chromanol glycoside (patent document 1). The present inventors have reported the utilization of edaravone, a cerebral neuroprotective drug, as a radiation protection drug (patent document 2 and non-patent document 2), the protective effect of nitroxides on radiation (non-patent document 3), and heat-treated yeasts containing minerals (patent document 3).

Patent Document 1: JP 10-72356 A
Patent Document 2: Japanese Patent Application No. 2002-67739
Patent Document 3: Japanese Patent Application No. 2005-379185
Non-Patent Document 1: Tsutomu Sugawara et al., "Houshasen to Igaku", Kyoritsu Shuppan Co., Ltd., 1986
Non-Patent Document 2: J. Radiat. Res, 45, 319-323 (2004)
Non-Patent Document 3: Free Radic. Biol. Med., 40, 1170-1178 (2006)

DISCLOSURE OF THE INVENTION

Problem to be Solved by the Invention

The present inventors found that ester derivatives of a tocopherol or a tocotrienol compound afford effective protection against radiation as a drug for effectively preventing health disorders (side effects) caused by exposure to radiation and radiodiagnosis or radiotherapy of cancer, whereby the present invention has been accomplished.

An object of the present invention is to provide an inexpensive drug for effective prevention and treatment of health disorders due to radiation in the case of exposure to radiation and diagnosis or therapy of cancer.

Means for Solving the Problem

That is, the present invention relates to the radioprotective effect of ester derivatives of a tocopherol or a tocotrienol compound.

More specifically, the present invention relates to use of a tocopherol or tocotrienol compound ester derivative represented by the general formula (1) or a pharmaceutically acceptable salt thereof for the manufacture of a drug for preventing, treating or reducing health disorders caused by exposure to radiation:

[Formula 1]

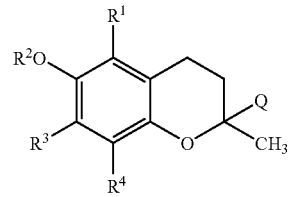

(1)

wherein Q is a group represented by

[Formula 2]

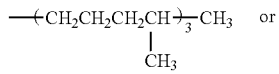

or

[Formula 3]

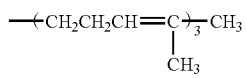

$R^1$ is a hydrogen atom or a methyl group,
$R^2$ is a group represented by
(i)

$R_2N(CH_2)_lCO-$  [Formula 4]

wherein each of Rs, which may be the same or different, is a hydrogen atom, a $C_{1-4}$ alkyl group or

[Formula 5]

$R_2^5N(CH_2)_mCO-$  (3)

(wherein each of $R^5$s, which may be the same or different, is a hydrogen atom or a $C_{1-4}$ alkyl group, and m is 0 to 3), and l is 1 to 4, (ii)

[Formula 6]

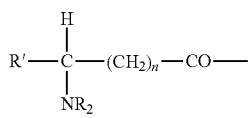

wherein n is 0 to 2, R is as defined above, and R' is a group selected from the group consisting of residues of alanine, arginine, valine, leucine, isoleucine, asparagine, aspartic acid, glutamine, glutamic acid, phenylalanine, methionine, cysteine, serine, threonine, tyrosine, proline, hydroxyproline, histidine and lysine, or (iii)

[Formula 7]

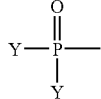
(4)

wherein each of Ys, which may be the same or different, is —OH, —O⁻, or —OA wherein A is an alkali metal, and each of $R^3$ and $R^4$, which may be the same or different, is a hydrogen atom or a $C_{1-4}$ alkyl group.

In addition, the present invention relates to a drug for preventing, treating or reducing health disorders caused by exposure to radiation which comprises a tocopherol or tocotrienol compound ester derivative represented by the general formula (1) or a pharmaceutically acceptable salt thereof:

[Formula 8]

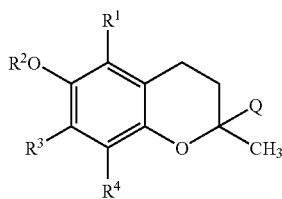
(1)

wherein Q is a group represented by

[Formula 9]

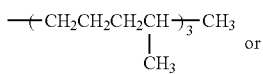 or

[Formula 10]

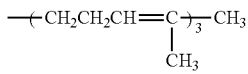

$R^1$ is a hydrogen atom or a methyl group, $R^2$ is a group represented by (i)

$R_2N(CH_2)_lCO—$      [Formula 11]

wherein each of Rs, which may be the same or different, is a hydrogen atom, a $C_{1-4}$ alkyl group or

[Formula 12]

$R_2^5N(CH_2)_mCO—$ (3)

(wherein each of $R^5$s, which may be the same or different, is a hydrogen atom or a $C_{1-4}$ alkyl group, and m is 0 to 3), and l is 1 to 4, (ii)

[Formula 13]

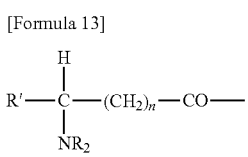

wherein n is 0 to 2, R is as defined above, and R' is a group selected from the group consisting of residues of alanine, arginine, valine, leucine, isoleucine, asparagine, aspartic acid, glutamine, glutamic acid, phenylalanine, methionine, cysteine, serine, threonine, tyrosine, proline, hydroxyproline, histidine and lysine, or (iii)

[Formula 14]

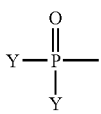
(4)

wherein each of Ys, which may be the same or different, is —OH, —O⁻, or —OA wherein A is an alkali metal, and each of $R^3$ and $R^4$, which may be the same or different, is a hydrogen atom or a $C_{1-4}$ alkyl group.

Furthermore, the present invention relates to a compound represented by the general formula (2), or a pharmaceutically acceptable salt thereof (preferably, hydrochloride):

[Formula 15]

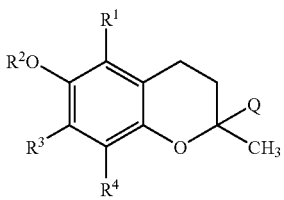
(2)

wherein Q is a group represented by

[Formula 16]

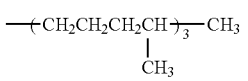

$R^1$ is a hydrogen atom or a methyl group,
$R^2$ is a group represented by (v)

[Formula 17]

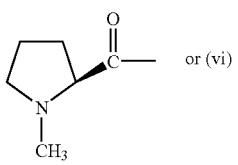 or (vi)

-continued

[Formula 18]

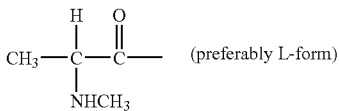

(preferably L-form)

and each of $R^3$ and $R^4$, which may be the same or different, is a hydrogen atom or a $C_{1-4}$ alkyl group.

When Q is

[Formula 19]

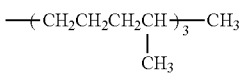

in the compound represented by the general formula (1) or (2), the compound is an aminoalkylcarboxylic acid ester derivative of a tocopherol.

When Q is

[Formula 20]

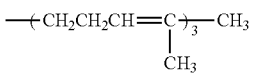

in the compound, the compound is an aminoalkylcarboxylic acid ester derivative of a tocotrienol compound.

The compound represented by the general formula (1) or (2) is preferably in d-form or dl-form.

In the formulas (i) and (ii), R is preferably a hydrogen atom, a methyl group or an ethyl group, more preferably a methyl group.

In the formula (ii), n is preferably 0 or 1.

The alanine, arginine, valine, leucine, isoleucine, asparagine, aspartic acid, glutamine, glutamic acid, phenylalanine, methionine, cysteine, serine, threonine, tyrosine, proline, hydroxyproline, histidine and lysine exemplified above as R' may be in any of D-form, L-form and DL-form, while they are preferably in L-form or DL-form.

While the pharmaceutically acceptable salt is not particularly limited, a typical example thereof is hydrochloride.

In the compound represented by the general formula (1) or (2), each of $R^3$ and $R^4$ is preferably a hydrogen atom or a methyl group, more preferably a methyl group.

In the group represented by the formula (4), Y is preferably —ONa.

"A Process for Producing an Ester of a Tocopherol or a Tocotrienol Compound and N,N-dimethylglycine, or its Hydrochloride"

Such a compound can be synthesized by the process described by Takata et al. in JP 1-121285 A, JP 2002-80475 A, non-patent document J. Lipid Res., 43, 2196 (2002), etc. For example, d-γ-tocopherol-N,N-dimethylglycine ester hydrochloride ($R^1$=$CH_3$, and $R^2$=N,N-dimethylaminoacetate hydrochloride) can be obtained by reacting d-γ-tocopherol with N,N-dimethylglycine hydrochloride in an amount of 1.2 moles per mole of d-γ-tocopherol and with dicyclohexylcarbodiimide in anhydrous pyridine at room temperature, isolating and purifying the reaction product by silica gel column chromatography, and converting the purified product to hydrochloride with hydrochloric acid-dioxane, followed by recrystallization.

"A Process for Producing an Amino Acid Ester Derivative of a Tocopherol or a Tocotrienol Compound"

Such an ester was synthesized by the process described in literature (non-patent document: Wakasugi K. et al., Tetrahedron Lett., 42, 7427-7430 (2001)). In acetonitrile are dissolved α- or γ-tocopherol (1 equivalent), a corresponding amino acid (1 equivalent; the amino group of cysteine is protected with a tertiary butoxycarbonyl group (($CH_3)_3$OCO—) and the thiol group is protected with a trityl group (($C_6H_5)_3$C—), N-methylalanine is protected with a tertiary butoxycarbonyl group, and N-methylproline and N,N-dimethylglycine are used without protection), N,N-dimethylbutylamine (3 equivalents) and 4-(dimethylamino)pyridine (1 equivalent), and a solution of dimethylsulfamoyl chloride (2 equivalents) in acetonitrile is added thereto with stirring. The reaction is carried out at 45-50° C. for 1 hour under an argon atmosphere. Water is added to the reaction solution, followed by extraction with ethyl acetate. The organic layer is washed with water and saturated aqueous sodium chloride solution and dried over magnesium sulfate. The solvent is distilled off and the residue is purified by a silica gel column chromatography (eluent: hexane/ethyl acetate) to obtain an ester (yield: 20-80%). The tertiary butoxycarbonyl group as protective group was removed by treatment with hydrochloric acid/ethyl acetate at 0° C. for 20 minutes and removal of the solvent by distillation to obtain hydrochloride (yield: 90%). The tertiary butoxycarbonyl group and trityl group for cysteine were removed by the method known in literature (non-patent document: Pearson D. A., et al., Tetrahedron Lett., 30, 2739-2742 (1989)), that is, they were removed by dissolution in methylene chloride and reaction with triethylsilane and trifluoroacetic acid at 0° C. for 1 hour. Ether was added to the reaction solution and the resulting mixture was washed with saturated aqueous sodium hydrogencarbonate solution and dried over magnesium sulfate. The solvent was distilled off and hydrochloric acid-ethyl acetate was added to the residue to obtain hydrochloride, after which the hydrochloride was isolated (yield: 30-55%) by a column chromatography (LH-20, eluent: methanol).

(1-3)d-γ-tocopherol-L-N-methylproline ester

IR ν max. (neat) 1751 cm−1; $[\alpha]_D$−34.4° (c=0.32, CHCl$_3$); $^1$H-NMR (CDCl$_3$); 0.79-0.89 (12H, m, —CH—CH$_3$), 0.95-1.60 (24H, m), 1.62-1.80 (2H, m, Ar—CH$_2$—CH$_2$—), 1.81-1.92 (1H, m), 1.92-1.99 (1H, m), 2.00 (3H, s, Ar—CH$_3$), 2.08 (3H, s, Ar—CH$_3$), 2.09-2.21 (1H, m), 2.21-2.46 (2H, m), 2.51 (3H, s, N—CH$_3$), 2.63-2.74 (2H, m, Ar—CH$_2$—), 3.14-3.26 (2H, m), 6.54 (1H, s, Ar—H); $^{13}$C-NMR (CDCl$_3$); 11.2, 12.7, 19.6, 19.7, 21.0, 22.2, 22.6, 22.7, 23.1, 24.2, 24.4, 24.8, 28.0, 29.9, 31.0, 32.7, 32.8, 37.3, 37.4, 39.4, 40.2, 40.8, 56.2, 67.5, 76.0, 118.4, 118.7, 125.8, 126.9, 141.4, 149.5, 172.6.

(1-3 hydrochloride)d-γ-tocopherol-L-N-methylproline ester hydrochloride

IR ν max. (CHCl$_3$) 1759 cm$^{-1}$; $[\alpha]_D$−11.4° (c 0.21, CHCl$_3$), melting point 138-143° C.;
$^1$H-NMR (CDCl$_3$); 0.78-0.91 (12H, m, —CH—CH$_3$), 0.95-1.86 (26H, m), 2.00 (3H, s, Ar—CH$_3$), 2.09 (3H, s, Ar—CH$_3$), 2.16-2.55 (3H, m), 2.70 (2H, t, J=6.8 Hz, Ar—CH$_2$—), 2.75-2.92 (1H, m), 3.01 (3H, s, N—CH$_3$), 3.21-3.45 (1H, m), 3.64-3.84 (1H, m), 4.52-4.73 (1H, m), 6.54 (1H, s, Ar—H), 13.42 (1H, brs); $^{13}$C-NMR (CDCl$_3$); 12.0, 12.7, 19.6, 19.7, 20.9, 22.1, 22.2, 22.6, 22.7, 24.1, 24.4, 24.8, 28.0, 29.2, 30.8, 32.7, 32.8, 36.5, 37.2, 37.4, 39.3, 40.1, 53.2, 64.0, 76.4, 118.0, 118.6, 126.2, 126.5, 140.2, 150.3, 167.3.

(1-4)d-α-tocopherol-L-N-methylproline ester

IR ν max. (neat) 1753 cm$^{-1}$; $[\alpha]_D$−30.9° (c 0.81, CHCl$_3$); $^1$H-NMR (CDCl$_3$): 0.79-0.90 (12H, m, —CH—CH$_3$), 0.97-1.60 (24H, m), 1.64-1.82 (2H, m, Ar—CH$_2$—CH$_2$—), 1.82-1.94 (1H, m), 1.96-2.02 (1H, m), 1.96 (3H, s, Ar—CH$_3$), 2.00 (3H, s, Ar—CH$_3$), 2.06 (3H, s, Ar—CH$_3$), 2.10-2.26 (1H, m), 2.26-2.45 (2H, m), 2.51 (3H, s, N—CH$_3$), 2.57 (2H, t, J=6.5 Hz, Ar—CH$_2$—), 3.17-3.29 (2H, m); $^{13}$C-NMR (CDCl$_3$): 11.8, 12.1, 13.0, 19.6, 19.7, 20.6, 21.0, 22.6, 22.7, 23.2, 23.9, 24.4, 24.8, 28.0, 30.0, 31.1, 32.7, 32.8, 37.3, 37.4, 39.4, 40.9, 56.3, 67.5, 75.0, 117.3, 123.0, 124.8, 126.6, 140.3, 149.4, 172.1.

(1-5 hydrochloride)d-γ-tocopherol-L-N-methylalanine ester hydrochloride

IR ν max. (nujol) 1765 cm$^{-1}$; [α]$_D$+7.4° (c 0.65, CHCl$_3$); melting point 141-145° C.; $^1$H-NMR (CDCl$_3$): 0.79-0.88 (12H, m, —CH—CH$_3$), 0.95-1.58 (24H, m), 1.60-1.80 (2H, m, Ar—CH$_2$—CH$_2$—), 1.85 (3H, d, J=6.6 Hz, N—CH—CH$_3$), 1.99 (3H, s, Ar—CH$_3$), 2.06 (3H, s, Ar—CH$_3$), 2.65 (2H, t, J=6.7, Ar—CH$_2$—), 2.79 (3H, s, NH—CH$_3$), 4.17 (1H, brs, NH—CH=CO), 6.63 (1H, s, Ar—H), 10.00 (1H, brs, NH); $^{13}$C-NMR (CDCl$_3$); 12.3, 13.2, 14.9, 20.0, 20.1, 21.4, 22.6, 23.0, 23.1, 24.4, 24.8, 25.2, 28.4, 31.1, 31.3, 33.1, 33.2, 37.7, 37.8, 39.8, 40.6, 56.5, 76.6, 118.9, 119.1, 126.4, 127.0, 141.1, 150.4, 168.2.

(1-6 hydrochloride)d-γ-tocopherol-L-cysteine ester hydrochloride

IR ν max. (CHCl$_3$) 1761 cm$^{-1}$; [α]$_D$+3.30° (c 1.1, CHCl$_3$); $^1$H-NMR (CDCl$_3$): 0.73-0.85 (12H, m, —CH—CH$_3$), 0.89-1.51 (24H, m), 1.51-1.77 (2H, m, Ar—CH$_2$—CH$_2$—), 1.90 (3H, s, Ar—CH$_3$), 1.97 (3H, s, Ar—CH$_3$), 2.48-2.66 (2H, m, Ar—CH$_2$—), 2.96-3.13 (1H, m, N—CH—CH$_2$—SH), 3.20-3.36 (1H, m, N—CH—CH$_2$—SH), 4.55 (1H, m, N—CH—CO), 6.58 (1H, s, Ar—H); $^{13}$C-NMR (CDCl$_3$): 11.9, 13.0, 19.6, 19.7, 21.0, 22.1, 22.6, 22.7, 23.8, 24.4, 24.8, 28.0, 30.9, 32.7, 32.8, 37.4, 39.3, 40.4, 55.7, 76.1, 118.7, 118.9, 125.9, 126.8, 140.9, 149.9, 167.1.

(1-7 hydrochloride)dl-α-tocopherol-L-cysteine ester hydrochloride

IR ν max. (CHCl$_3$) 1759 cm$^{-1}$; $^1$H-NMR (CDCl$_3$): 0.79-0.88 (12H, m, —CH—CH$_3$), 0.95-1.60 (24H, m), 1.62-1.80 (2H, m, Ar—CH$_2$—CH$_2$—), 1.93 (3H, s, Ar—CH$_3$), 1.96 (3H, s, Ar—CH$_3$), 2.02 (3H, s, Ar—CH$_3$), 2.45-2.57 (2H, m, Ar—CH$_2$—), 3.06-3.21 (1H, m, N—CH—CH$_2$—SH), 3.28-3.42 (1H, m, N—CH—CH$_2$—SH), 4.56 (1H, m, N—CH—CO); $^{13}$C-NMR (CDCl$_3$): 11.8, 12.5, 13.3, 19.5, 19.6, 19.7, 20.6, 21.0, 22.6, 22.7, 24.5, 24.8, 25.1, 28.0, 30.8, 31.1, 32.7, 32.8, 37.3, 37.4, 37.5, 37.6, 39.4, 55.1, 75.2, 117.6, 123.2, 124.9, 126.5, 140.1, 149.8, 167.1.

(1-8)d-γ-tocopherol-N-dimethylglycinyl-L-alanine ester

IR ν max. (CHCl$_3$) 1759, 1680 cm$^{-1}$; [α]$_D$−17.2° (c 0.36, CHCl$_3$); $^1$H-NMR (CDCl$_3$): 0.78-0.90 (12H, m, —CH—CH$_3$), 0.96-1.82 (26H, m), 1.54 (3H, d, J=7.2, NH—CH$_3$), 2.00 (3H, s, Ar—CH$_3$), 2.08 (3H, s, Ar—CH$_3$), 2.31 (6H, s, NH—(CH$_3$)$_2$), 2.68 (2H, t, J=6.3, Ar—CH$_2$—), 2.90-3.07 (2H, m, N(CH$_3$)$_2$—CH$_2$—CO), 4.87 (1H, dt, J=7.2, 8.1, NH—CH—CO), 6.56 (1H, s, Ar—H), 7.62 (1H, d, J=8.1, CO NH—CH—CH$_3$);
$^{13}$C-NMR (CDCl$_3$): 11.9, 12.6, 18.4, 19.6, 19.7, 21.0, 22.2, 22.6, 22.7, 24.2, 24.4, 24.8, 26.3, 28.0, 31.0, 32.7, 32.8, 37.4, 39.4, 40.2, 45.9, 47.5, 62.9, 76.1, 118.5, 118.6, 125.9, 126.9, 141.2, 149.7, 170.5, 172.2.

"A Process for Producing a Phosphoric Ester Derivative of a Tocopherol"

dl-α-Tocopherol phosphate disodium salt is obtained by the method described in literature (Gianello R., et al., Free Radical Biology and Medicine, 39, 970-976 (2005)) or is available as a commercial product. The commercial product was used in the experiment described hereinafter.

dl-γ-Tocopherol phosphate disodium salt was synthesized as follows.

In t-butyl methyl ether-pyridine (10:1) is dissolved d-γ-tocopherol, and phosphoryl chloride (POCl$_3$) is added thereto in an amount of 2 moles per mole of d-γ-tocopherol. Under ice-cooling, 15% aqueous sulfuric acid solution is added thereto to effect separation. To the t-butyl methyl ether layer is added 35% aqueous sulfuric acid solution, and the resulting mixture is refluxed at 70° C. for 7 hours. The t-butyl methyl ether layer is washed with water and adjusted to pH 8.9 with 5% solution of sodium hydroxide in methanol. The t-butyl methyl ether layer is concentrated under reduced pressure and acetone is added thereto. The precipitate formed is collected by filtration, dried and then washed with methanol to obtain the desired compound.

MS (FAB+) m/z 541 ([M+H]); $^1$H-NMR (CD$_3$OD): 0.89-0.85 (12H, m), 1.77-1.05 (26H, m, including 1.22 (3H, s)), 2.05 (3H, s), 2.19 (3H, s), 2.71 (2H, t), 7.13 (1H, s).

The tocopherol or tocotrienol compound ester derivative according to the present invention is a safe substance, and LD$_{50}$ of γ-tocopherol-N,N-dimethylglycine ester hydrochloride in the case of single oral administration to rats is 2000 mg/Kg or more.

In the case of temporary whole-body exposure to radiation expected owing to an accident or the like and temporary exposure to radiation in radiotherapy of cancer, such a drug is administered immediately before or after the radiation exposure. In the case of radiation exposure due to an unexpected accident or the like, the drug is administered immediately after the radiation exposure. The tocopherol or tocotrienol compound ester derivative may be orally administered in the form of tablets, capsules or an aqueous solution or may be administered by intraperitoneal or subcutaneous injection after having been suspended in a pharmacologically acceptable medium such as water, physiological saline or methylcellulose.

The dose of the tocopherol or tocotrienol compound ester derivative is preferably 10-300 mg/Kg in the case of temporary exposure to radiation. The derivative is preferably administered in a dose of 5-100 mg/Kg at intervals of several hours in the case of long-term exposure to radiation.

EXAMPLES

The present invention is specifically illustrated with reference to the following examples, which should not be construed as limiting the scope of the invention.

Example 1

Seven to thirteen male C3H mice aged 10 weeks (body weight: 25-28 g) per group were irradiated with X-rays (7.5-8.5 Gy) and their survival rate was determined 30 days after the irradiation. To each of drug-treated groups was intraperitoneally or subcutaneously administered 0.5% methylcellulose solution (0.3 ml) containing d-γ-tocopherol-N,N-dimethylglycine ester hydrochloride in an amount of 10-300 mg/Kg, before or after the irradiation. To a control group was intraperitoneally administered 0.5% methylcellulose solution in a volume of 0.3 ml per mouse.

TABLE 1

| | Dose (mg/kg body wt. i.p. administration * S.C. administration) | Irradiation dose (Gy) | Administration timing | Number of test mice | Survival rate after 30 days (%) |
|---|---|---|---|---|---|
| Control group (0.5% methylcellulose) | | 7.5 | Immediately after irradiation | 60 | 7 |
| d-γ-Tocopherol-N,N-dimethylglycine ester hydrochloride | 10 | 7.5 | Immediately after irradiation | 10 | 10 |
| | 20 | 7.5 | Immediately after irradiation | 30 | 60 |
| | 50 | 7.5 | Immediately after irradiation | 20 | 85 |
| | 100 | 7.5 | Immediately after irradiation | 42 | 98 |
| | 300 | 7.5 | Immediately after irradiation | 22 | 55 |
| | 100 | 7.5 | 30 min. before irradiation | 10 | 60 |
| | 100 | 7.5 | Immediately before irradiation | 10 | 80 |
| | 100 | 7.5 | Immediately after irradiation | 42 | 98 |
| | 100 | 7.5 | 1 hr. after irradiation | 17 | 88 |
| | 100 | 7.5 | 10 hrs. after irradiation | 20 | 75 |
| | 100 | 7.5 | 24 hrs. after irradiation | 20 | 40 |
| | 100* | 7.5 | Immediately after irradiation | 13 | 85 |
| | 100 | 8 | Immediately after irradiation | 18 | 78 |
| | 100 | 8.5 | Immediately after irradiation | 19 | 37 |

Example 2

Eight to eleven male C3H mice aged 10 weeks (body weight: 25-28 g) per group were irradiated with X-rays (7.5 Gy) and their survival rate was measured 30 days after the irradiation. To drug-treated groups was intraperitoneally administered 0.5% methylcellulose solution (0.3 ml) containing d-α-tocopherol-N,N-dimethylglycine ester hydrochloride, d-γ- or d-α-tocotrienol-N,N-dimethylglycine ester hydrochloride, d-γ- or dl-α-tocopherol phosphate disodium salt, or d-γ-tocopherol-N-methyl-L-proline ester hydrochloride, respectively, in an amount of 100 mg/Kg, immediately after the irradiation. To a control group was intraperitoneally administered 0.5% methylcellulose solution in a volume of 0.3 ml per mouse.

TABLE 2

| | Dose (mg/kg body wt.) | Irradiation dose (Gy) | Administration timing | Number of test mice | Survival rate after 30 days (%) |
|---|---|---|---|---|---|
| Control group (0.5% methylcellulose) | | 7.5 | Immediately after irradiation | 60 | 7 |
| d-α-Tocopherol-N,N-dimethylglycine ester hydrochloride | 100 | 7.5 | Immediately after irradiation | 21 | 95 |
| d-γ-Tocotrienol-N,N-dimethylglycine ester hydrochloride | 100 | 7.5 | Immediately after irradiation | 20 | 85 |
| d-α-Tocotrienol-N,N-dimethylglycine ester hydrochloride | 100 | 7.5 | Immediately after irradiation | 21 | 91 |
| d-γ-Tocopherol phosphate disodium salt | 100 | 7.5 | Immediately after irradiation | 20 | 70 |
| dl-α-Tocopherol phosphate disodium salt | 100 | 7.5 | Immediately after irradiation | 15 | 40 |
| d-γ-Tocopherol-N-methyl-L-proline ester hydrochloride (1-3, hydrochloride) | 100 | 7.5 | Immediately after irradiation | 10 | 90 |

The above results indicate that the tocopherol or tocotrienol compound ester derivative effectively prevents health disorders caused by exposure to radiation and has therapeutic effect on the health disorders.

The invention claimed is:

1. A method for treating or reducing side effects caused by exposure to radiotherapy or radiodiagnosis, which comprises administering to a patient in need thereof, a therapeutically effective amount of a compound represented by the general formula (I) or a pharmaceutically acceptable salt thereof:

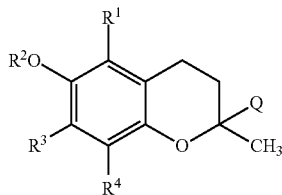
(1)

wherein Q is a group represented by formula

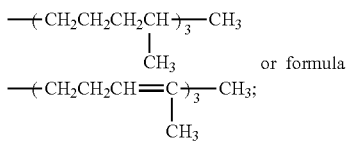
or formula $R^1$ is a methyl group;
$R^2$ is a group (i) represented by general formula:

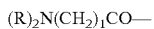

(wherein each of the two Rs, which may be the same or different, is a hydrogen atom or a $C_{1-4}$ alkyl group, and l is 1 to 4), or

(3)

(wherein each of the two $R^5$s, which may be the same or different, is a hydrogen atom or a $C_{1-4}$ alkyl group, and m is 0 to 3);
a group (ii) represented by general formula:

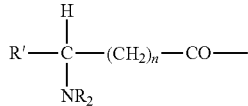

(wherein n is 0 to 2, R is as defined above, and R' is a side chain of an amino acid selected from the group consisting of alanine, arginine, valine, leucine, isoleucine, asparagine, aspartic acid, glutamine, glutamic acid, phenylalanine, methionine, cysteine, serine, threonine, tyrosine, proline, hydroxyproline, histidine and lysine); or
a group (iii) represented by general formula:

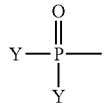
(4)

(wherein each of the two Ys, which may be the same or different, is —OH, —O⁻, or —OA wherein A is an alkali metal); and
each of $R^3$ and $R^4$, which may be the same or different, is a hydrogen atom or a $C_{1-4}$ alkyl group.

2. The method as claimed in claim 1, wherein said compound represented by the general formula (I) is d-α-tocopherol N,N-dimethylglycine ester, d-γ-tocotrienol N,N-dimethylglycine ester, d-α-tocotrienol N,N-dimethylglycine ester, d-γ-tocopherol phosphate disodium salt, dl-α-tocopherol phosphate disodium salt, or d-γ-tocopherol N-methyl-L-proline ester.

* * * * *